United States Patent [19]

Wallace

[11] 4,308,627

[45] Jan. 5, 1982

[54] PROCESS FOR PREVENTION OF CHALKBROOD DISEASE

[76] Inventor: Melvin W. Wallace, 611 E. Ustick, Caldwell, Id. 83605

[21] Appl. No.: 176,478

[22] Filed: Aug. 8, 1980

[51] Int. Cl.$^3$ ............................................. A01K 51/00
[52] U.S. Cl. ..................................... 6/12 M; 424/228
[58] Field of Search ......................... 6/12 M; 424/228; 260/397.6

[56] References Cited

U.S. PATENT DOCUMENTS

| 2,973,298 | 2/1961 | Goldhaft et al. | 424/228 |
| 3,555,055 | 1/1971 | Kaplan | 424/228 X |
| 4,234,986 | 11/1980 | Cox et al. | 6/12 R |

FOREIGN PATENT DOCUMENTS 19057 of 1912 United Kingdom ................. 6/12 M

*Primary Examiner*—Gene Mancene
*Assistant Examiner*—Robert P. Swiatek
*Attorney, Agent, or Firm*—Paul F. Horton

[57] ABSTRACT

Process for the prevention of chalkbrood disease amongst leafcutter bees (Megachile species) including the step of dusting the entrance of nesting holes with sodium sulfathiazole whereby incoming bees must come in contact with the powder upon entering the hole. Where old, previously used, beeboards are used as nesting holes, the process includes cleaning debris from the nesting holes and scouring the board with a dilute solution of calcium hypochlorite before applying the sodium sulfathiazole.

7 Claims, No Drawings

PROCESS FOR PREVENTION OF CHALKBROOD DISEASE

BACKGROUND OF THE INVENTION

1. Field of the Invention

This invention relates to the process of preventing chalkbrood disease amongst leafcutter bees.

2. Description of the Prior Art

Alfalfa seed production is an important industry in the western United States. In recent years, production has increased significantly, primarily because of use of the alfalfa leafcutter bee (Megachilidae family, Megachile rotundata) as a pollinator. Management of the bees has, in itself, become a large and profitable business.

Since the year 1975, however, the leafcutter bees have been increasingly threatened by a contagious disease known as chalkbrood caused by a fungus (Ascosphaera sp.) which spreads by microscopic spores. The disease has cost alfalfa seed growers millions of dollars annually. In the state of Idaho, alone, losses for the year 1979 were approximately six million dollars as a result of an approximately 20 percent decline in leafcutter bee population due to the disease.

The chalkbrood disease turns the body of an infected bee larva almost completely into fungal cells which eventually produce millions of spores. The destroyed larvae, remaining in large part in the nesting holes, serve as primary sources of infection.

As a result of the large loss in seed production, a massive research program has been launched by entomologists. Researchers have tried controlling the disease with various fungicides, with ultraviolet rays and with other forms of radiation, without success. The latest method and probably most practical method, to date, is the bathing of bees in a 1% solution of chlorox. The primary disadvantage of this method is the loss of from 5 to 30% of the bees by either drowning or poisoning. The disease is further prevented, in part, by placing nesting boards in an area protected from the weather, providing proper ventilation and placing boards in a cool, shady area.

Of prior art patents, U.S. Pat. No. 3,775,786 issued to C. Reinert, would appear most relevant.

It is known that tetracycline and sulfathiazole have been used in controlling a disease common amongst honeybees (family Apidae, *Apis mellifera*); a disease known as American Foulbrood disease. Foulbrood disease, unlike chalkbrood disease, is caused by aerobic bacteria known as *Bacillus larvae*.

SUMMARY OF THE INVENTION

It is a general object of the present invention to provide a process for the prevention of chalkbrood disease amongst bees of the family Megachilidae. The process has been carried out with great success by dusting the nesting holes of leafcutter bees with sodium sulfathiazole, requiring any bee entering a nesting hole to come into contact with the chemical agent. Where used beeboards are used as nesting holes, the process includes removing debris from the holes and scouring the board with a solution of (chlorox).

DETAILED DESCRIPTION OF THE INVENTION

Chalkbrood disease is spread by adult bees. Infectious spores adhere to the body of the adult bee in the bee's contact with material within the nesting hole. Spores are continuously picked up and released as the bees fly from the field to the nesting hole carrying leaf material, nectar, and pollen.

It has been found quite unexpectedly by applicant that chemicals from the class known generally as sulfa drugs are extremely effective in controlling the disease. While sulfa drugs are well known for their inhibition of bacterial growth, use as a fungicide or inhibitor of fungi, particularly the fungus ascosphaera, was hitherto unknown. Sulfa drugs are synthetic organic compounds, such as sulfathiazole and sulfadiazine, and are chemically similar to sulfonamide. Experiments were largely performed with the sulfa drug, sodium sulfathiazole, as used with beeboard management of leafcutter bees, and therefore the process described will be restricted to that description although it will be understood that use of other sulfa drugs and nesting hole materials are closely related.

When using previously used bee houses, phase-out houses, and beeboards, all units should be thoroughly washed and scrubbed with soap and water for the removal of existing debris including dead larvae, leaf material, and infectious spores. After the units have dried, they are scoured with a solution of calcium hypochlorite, well known under the trademark Clorox. If the bee house or phase-out house is then painted, they should again be scoured with Clorox and allowed to dry.

Empty bee boards, including new un-used boards and used boards previously cleaned and treated as above described, are then laid down so that the entrance holes are facing upward. Sodium sulfathiazole, in powder form, is then sprinkled over the board and, by means of a whisk broom, each hole is provided with the powder for a depth of approximately one-half to three-quarters of an inch. The boards are then carefully handled as they are placed in an upright position for nesting within the bee house to prevent spillage of the powder from the holes. It is essential that sufficient sulfathiazole remain in each hole that the adult bee receives a good dust bath as she cleans the hole for nesting. It is to be noted, in this regard, that the sulfathiazole is for treatment of the bee, not the board which has, if not new, already been sterilized. It is also to be noted that the present process is effective with a variety of nesting materials, all labeled herein as "beeboards", but including new paper soda straws, wooden boards with drilled holes, grooved laminated boards, and the more recently used grooved laminated molded plastic sheets.

After the beeboards have become filled with larvae, they are taken from the bee house and placed in the phase-out house for incubation. The phase-out house is preferably maintained within the temperature range of 75°–90° for optimum results. Sodium sulfathiazole is generously sprinkled in front of the exit hole of the phase-out house and along the base of the parasite trap so that any emerging bees will get a proper dust bath. The above described process is to be faithfully repeated for each hatch.

It is to be appreciated and will be apparent to those skilled in the art that slight changes made be made in the process without altering the inventive concepts embodied therein. The described process is therefore to be considered as illustrative and not restrictive, the scope of the invention being indicated by the appended claims rather than the foregoing description, and all changes which come within the meaning and range of equivalency of the claims are therefore to be embraced therein.

I claim:

1. A process for treating leafcutting bees to prevent the spread of chalkbrood disease comprising the placing into the entrance of the bees' nesting hole a chemical agent from the sulfa drug class in such a manner that the bee must contact the chemical upon entering the hole.

2. The process as described in claim 1 wherein said chemical is in powder form.

3. The process as described in claim 2 wherein said chemical agent is sodium sulfathiazole.

4. In the use of beeboards for nesting holes, a process for treating leafcutting bees to prevent the spread of chalkbrood disease comprising the dusting of the entrance to the beeboard holes with a powder from the sulfa drug class so that a bee entering one of the holes must contact the powder upon entering the hole.

5. The process as described in claim 4 wherein said powder includes the chemical agent sodium sulfathiazole.

6. In the use of previously used beeboards, a process for the prevention of chalkbrood disease comprising the removal of foreign material from the holes of the beeboard; scouring the beeboard with a solution of calcium hypochlorite; drying the beeboard; and the placement into the entrance of bees' nesting holes within the beeboard of a sulfa drug powder in such a manner that any bee entering a hole is required to contact the sulfa drug powder upon entering the hole.

7. The process as described in claim 6 wherein said sulfa drug is sodium sulfathiazole.

* * * * *